US 7,417,730 B2

(12) United States Patent
Duan et al.

(10) Patent No.: US 7,417,730 B2
(45) Date of Patent: Aug. 26, 2008

(54) APPARATUS AND METHOD FOR MONITORING BREATH ACETONE AND DIABETIC DIAGNOSTICS

(75) Inventors: Yixiang Duan, Los Alamos, NM (US); Wenqing Cao, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/395,733

(22) Filed: Mar. 31, 2006

(65) Prior Publication Data

US 2007/0229818 A1  Oct. 4, 2007

(51) Int. Cl.
*G01N 21/73* (2006.01)
(52) U.S. Cl. ...................................... 356/316
(58) Field of Classification Search ................. 356/316
See application file for complete search history.

(56) References Cited

U.S. PATENT DOCUMENTS

| 6,429,935 | B1 | 8/2002 | Duan |
| 6,734,964 | B1 | 5/2004 | Duan et al. |
| 6,900,734 | B2 | 5/2005 | Duan |
| 2005/0195393 | A1* | 9/2005 | Karanassios ................. 356/316 |

FOREIGN PATENT DOCUMENTS

WO   WO 02/44698 A1 *  6/2002

OTHER PUBLICATIONS

Hyland et al.,Gas recognition using a neural network approach to plasma optical emission spectroscopy, Proceedings of SPIE, vol. 4120, 2000, pp. 246-252.*
Mariotti et al., Experimental study of breakdown voltage and effective secondary electron emission coefficient for a micro-plasma device, Plasma Sources Science and Technology, vol. 13, 2004, pp. 207-212.*
Rooth et al., "Acetone in Alveolar Air, and the Control of Diabetes", The Lancet, Nov. 1966, pp. 1102-1105.
Tassopoulos et al., "Breath-Acetone and Blood-Sugar Measurements in Diabetes", The Lancet, Jun. 1999, pp. 1282-1286.
Phillips et al., "Variation in Volatile Organic Compounds in the Breath of Normal Humans," J. Chromatogr. Jun. 1999, vol. 729, pp. 75-88.
Smith et al., "Trace Gases in Breath of Healthy Volunteers When Fasting and After a Protein-Calorie Meal: a Preliminary Study," J. Appl Physiol., Nov. 1999, vol. 87, pp. 1584-1588.
Jin et al., "A Low-Power, Atmospheric Pressure, Pulsed Plasma Source for Molecular Emission Spectrometry", Anal. Chem., Jan. 2001, vol. 73, pp. 360-365.

(Continued)

*Primary Examiner*—F. L Evans
(74) *Attorney, Agent, or Firm*—Samuel L. Borkowsky (57) ABSTRACT

An apparatus and method for monitoring diabetes through breath acetone detection and quantitation employs a microplasma source in combination with a spectrometer. The microplasma source provides sufficient energy to produce excited acetone fragments from the breath gas that emit light. The emitted light is sent to the spectrometer, which generates an emission spectrum that is used to detect and quantify acetone in the breath gas.

6 Claims, 7 Drawing Sheets

OTHER PUBLICATIONS

Duan et al., "Capillary-Discharged-Based Portable Detector for Chemical Vapor Monitoring", Review of Scientific Instruments, May 2003, vol. 74, No. 5, pp. 2811-2816.

Sanchez et al., "GC Analysis of Human Breath with A Series-Coupled Column Ensemble and a Multibed Sorption Trap", Anal. Chem., May 2003, vol. 75, pp. 2231-2236.

Jin et al., "Simple, Sensitive Nitrogen Analyzer Based on Pulsed Miniplasma Source Emission Spectrometry", Review of Scientific Instruments, Dec. 2003, vol. 74, No. 12, pp. 5156-5160.

Wang et al., "Measurements of Cavity Ringdown Spectroscopy of Acetone in the Ultraviolet and Near-Infrared Spectral Regions: Potential for Development of a Breath Analyzer", Applied Spectroscopy, Jul. 2004, vol. 58, No. 7, pp. 784-791.

* cited by examiner

APPARATUS AND METHOD FOR MONITORING BREATH ACETONE AND DIABETIC DIAGNOSTICS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to breath acetone and diabetes and more particularly to an apparatus and method for monitoring breath acetone noninvasively.

BACKGROUND OF THE INVENTION

Diabetes is a disorder of metabolism in the way the body uses digested food for growth and energy. From a medical point of view, diabetes is regarded as a disease in which an absolute or relative inadequacy of insulin effect gives rise to a complex disturbance of metabolism that is dominated by an increase of glucose levels and/or intensive lipolysis. Because glucose is not a readily available energy source in the case of insulin deficiency, ketones are produced as an alternative energy source. Ketones, also known in the art as "ketone bodies," are chemicals that the body makes when there is not enough insulin in the blood. Ketones (acetone, for example) build up in the blood and the body can remove them in the urine. The gas phase acetone in the bloodstream equilibrates with alveolar air (exhaled air) through the alveoli, and the concentration of acetone in breath can reflect metabolic products of diabetes in some way. The body can rid itself of acetone through the lungs, which gives the breath a fruity odor. If a large amount of acetone forms and passes through the body into the blood, urine, and breath, it usually means that the cells either do not have enough insulin, or cannot use the insulin in the proper way. Ketone bodies are produced by the liver and used peripherally as an energy source when glucose is not readily available.

Figure 1:
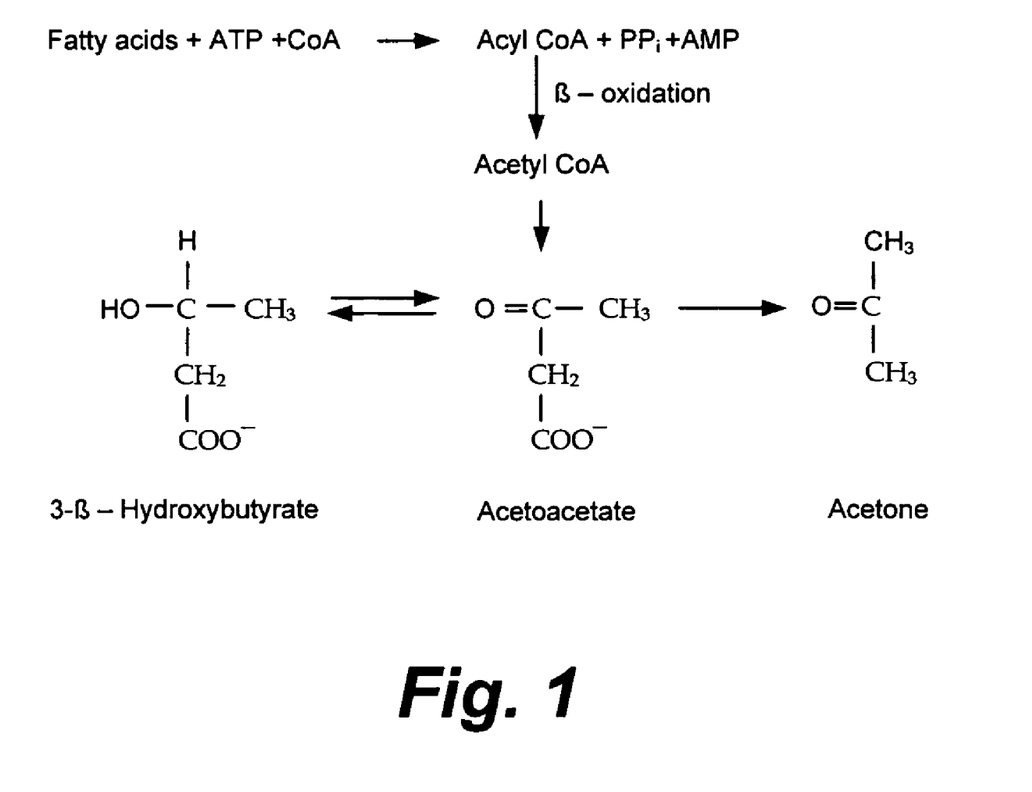
FIG. 1 shows a mechanistic scheme believed to be involved in the production of ketone bodies.

Ketones are always present in the blood and their levels increase with diabetes, which is the most common pathological cause of elevated blood ketones. Ketones include the molecules acetoacetate (AcAc), 3-β-hydroxybutyrate (3HB), and acetone. In diabetic ketoacidosis (DKA), high levels of ketones are produced in response to low insulin levels. As shown in FIG. 1, AcAc accumulates during fatty acid metabolism under low carbohydrate conditions. 3HB is formed from the reduction of AcAc in the mitochondria. These two predominant ketones are energy rich compounds that transfer energy from the liver to other tissues. Acetone is generated by spontaneous decarboxylation of AcAc and is responsible for the sweet odor on the breath of individuals with ketoacidosis.

Diabetes is a large and growing problem throughout the world. The World Health Organization reported that the global diabetic number was 171 million for the year 2000 and assessed the number for the year 2030 would be 336 million. In the United States, 18.2 million people are estimated to have diabetes problems. Persons with diabetes are at increased risk for debilitating complications such as renal failure, blindness, nerve damage, and vascular disease. The number of diabetes cases in the United States is increasing at about 5 percent each year, and ranked as the sixth leading cause of death and disability, at a cost of 132 billion dollars per year. Demand for monitoring and diabetes diagnostic products is projected to advance over 8 percent annually to 4.4 billion dollars in 2008.

Currently available methods for primary screening and diagnostic tests of diabetes are generally inconvenient and unpleasant. Fast Plasma Glucose (FPG), and the Oral Glucose Tolerance Test (OGTT), for example, require venous draws and are fasting-based tests, so they can only be practically administered during morning appointments. For OGTT, the measurement is performed about 2 hours after the patient ingests a 75-gram oral glucose load. Numerous studies have evaluated the performance of these methods in diverse populations. Specificity (correctly identifying absence of disease) of FPG test exceeds 96 percent, but the sensitivity (correctly identifying disease) is only on the order of about 50 percent. Thus, approximately half of those with diabetes may be misclassified by a single FPG test. The sensitivity and specificity for OGTT are 73 percent and 80 percent, respectively, but the test suffers from relatively poor reproducibility (coefficient and variation of about 17 percent). Moreover, glucose self-monitoring is typically done by pricking a finger and extracting a drop of blood with a test strip composed of chemicals sensitive to glucose. In order to strictly control glucose and effectively mitigate the complications, 4-7 tests per day are recommended for diabetes patients. Due to the physical suffering and daily cost, this type of diabetic testing can be carried out usually at a rate of twice a day. Because of all of these restrictions, scientists have been trying to find effective noninvasive ways for diabetes monitoring through measuring blood glucose. For this purpose, a huge sum of funds and manpower have been invested to develop various noninvasive technologies including, for example, Raman spectroscopy, infrared spectroscopy, near infrared spectroscopy, photoacoustic spectroscopy, light scattering, and polarization changes. So far, none of these technologies achieves a satisfactory level for practical applications.

The detection of volatile organic compounds (VOCs) in breath for the purpose of medical diagnosis has a long history. Ancient Greek physicians knew that the aroma of human breath could provide clues to medical diagnosis. The astute physician was alert for the sweet fruity odor of acetone in a patient's breath with uncontrolled diabetes, the musty fishy reek of advanced liver disease, the urine-like smell that accompanies failing kidneys, and the putrid stench of a lung abscess.

Modern breath analysis began in the 1970's when Pauling and others identified more than 200 components in human breath using gas chromatography. Since then, issues concerning the physiological meaning of the breath substances and correlations of breath markers with patients' clinical conditions have become more and more important. Since the 1990's, researchers have been trying to understand the relationship between various breath substances and the body's physical condition. Among the chemicals identified in breath gas, it has been shown that acetone is correlated with blood glucose as an alternative biomarker for diabetes. In healthy individuals, breath acetone is at the level of a few hundred ppbv, whereas diabetics have a broader range of breath acetone concentration of hundreds or even thousands of ppm, depending mainly on physical properties of individuals and the level of blood glucose of patients. The composition of VOCs in breath varies widely from person to person, and includes at least hundreds of compounds. The concentration of acetone in breath can be as low as a few hundred ppbv, making accurate analysis of breath acetone a significant challenge.

A current test for breath acetone is carried out using gas chromatography (GC) coupled with a detection method such as mass spectroscopy (MS) or flame ionization. These methods require bulky equipment and skilled operators, and are time consuming with regard to sample collection, transportation, storage, and separation, and therefore are not suitable for outside laboratory applications such as daily monitoring and prescreening diagnosis of diabetes. In addition, the trace amounts of acetone that are present in the breath may easily be lost during these complex procedures because acetone is a volatile and chemically active material. Some other methods, such as light addressable potentiometric sensors and electronic nose, are less selective for particular components, and therefore, potential interference of the breath matrix gas on acetone detection is unavoidable.

Recently, cavity ringdown spectroscopy was used for detecting acetone at ultraviolet and near-infrared wavelength ranges. Although a detection limit of 1.5 ppmv for acetone vapor was reported, the moisture in breath gas may impact sensitivity because the reflectivity of the cavity mirrors is prone to the humidity in breath, and it is difficult to completely filter out the large amount of water vapor in breath without influencing the trace amount of acetone because acetone is miscible with water in almost any ratio. The added cost of the laser used in this system may be an extra issue for the desirable features in breath analysis.

A reported method for determining acetone in breath is based on the reaction of acetone with alkaline salicylaldehyde to form a colored product that absorbs in the blue region and can be monitored with gallium nitride-based light emitting diodes (LEDs) with an emission centered at 465 nm. The method achieved a detection limit as low as 14 ppbv for acetone. However, memory effects of the reaction system and trace loose acetone are potential problems for the technique in real breath sample analysis.

SUMMARY OF THE INVENTION

In accordance with the purposes of the present invention, as embodied and broadly described herein, the present invention includes an apparatus comprising a sampling line for injecting a sample of breath gas therein, a microplasma source in communication with the sampling line for fragmenting compounds in the injected breath gas to compound fragments, and a spectrometer in communication with the microplasma source for providing a light emission spectrum from the compound fragments.

The invention also includes a method for monitoring breath gas comprising using a plasma to fragment compounds in a sample of breath gas to produce compound fragments that emit light, and directing at least a portion of light emitted from compound fragments to a spectrometer.

The invention also includes a method for monitoring breath acetone comprising fragmenting a sample of breath gas in a plasma to produce compound fragments that emit light, directing at least a portion of the emitted light to a spectrometer, using the spectrometer to produce a spectrum of the emitted light, and using the spectrum of the emitted light to determine the amount of breath acetone in the sample.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The invention is concerned with an apparatus and method for the noninvasive monitoring of diabetes through breath acetone analysis. The invention uses a microplasma discharge in combination with a small spectrometer for highly sensitive detection of breath acetone. In contrast to invasive methods such as those involving finger pricking to draw blood, the present invention is noninvasive, and a patient may use the invention as an aid in controlling their diabetes and also in diet control, drug therapy, and lifestyle changes. Thus, the invention can be used without any discomfort or physical pain to the patient.

An embodiment apparatus was calibrated using an acetone gas standard, and tested using real human breath. A detection limit in the low ppbv level for breath acetone was achieved. This low level is sufficient for monitoring the health and diabetes of individuals.

Reference will now be made in detail to the present preferred embodiments of the invention. Similar or identical structure is identified using identical callouts.

Figure 2:
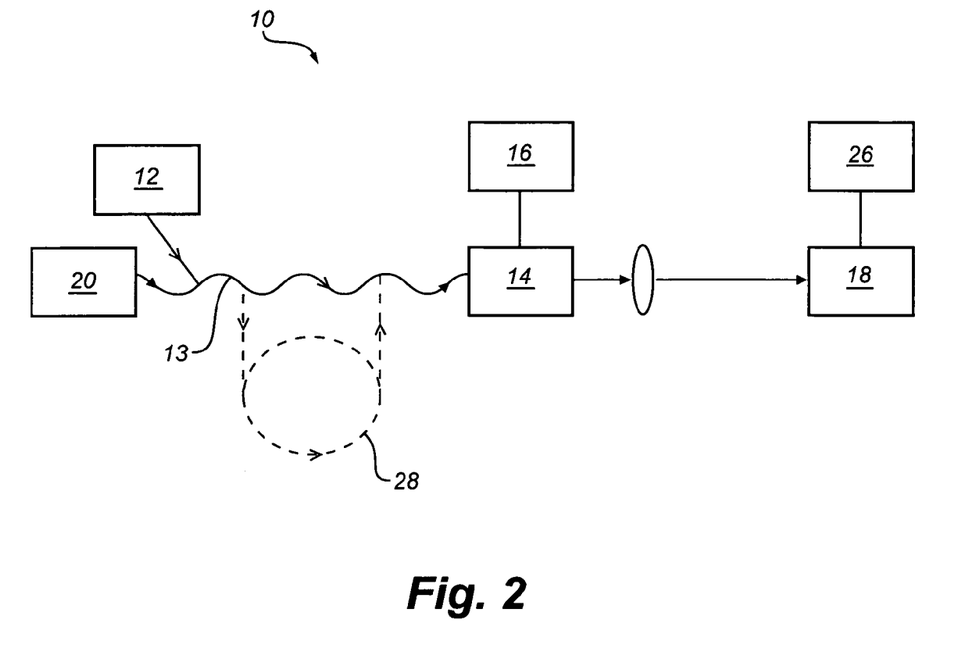
FIG. 2 shows a schematic diagram of an embodiment apparatus for monitoring breath acetone.

A schematic diagram of an embodiment apparatus of the invention is shown in FIG. 2. Apparatus 10 includes syringe injector 12 for introducing a sample of breath into apparatus 10. Apparatus 10 also includes microplasma source 14 for fragmenting acetone into acetone fragments and exciting the acetone fragments along with unfragmented acetone. Power supply system 16 (preferably a small one) supplies energy needed for generating and sustaining the microplasma of microplasma source 14. Spectrometer 18 (preferably a small one) produces spectra from the emission of the excited materials produced in microplasma source 14. During operation, a sample is injected into apparatus 10, combines with supply gas 20 in sampling line 13, and moves through sampling line 13 and into microplasma source 14. An optical emission beam generated from excited materials produced in microplasma source 14 is collected using, for example, collimating lens 22, and is transmitted through optical fiber 24 to spectrometer 18. A programmable computer 26 may be used to process the spectral data obtained from spectrometer 18. Optionally, separator 28 (a capillary tube, for example) may be used in between injector 12 and microplasma source 14 for removing and/or separating components from a sample before they reach microplasma source 14. The optional separation step may be needed to prevent certain components from interfering with the acetone detection. In practice, a small collimating lens with a diameter of about 5-mm was used to collect emission beams from the plasma and focus the beams into an optical fiber or lens. A high-resolution, palm-sized spectrometer, coupled with a small linear charge coupled detector (CCD) array, may be used for spectrum measurement and detection. Computer software with advanced acquisition and display function was used for data collection and storage.

Figure 3A:
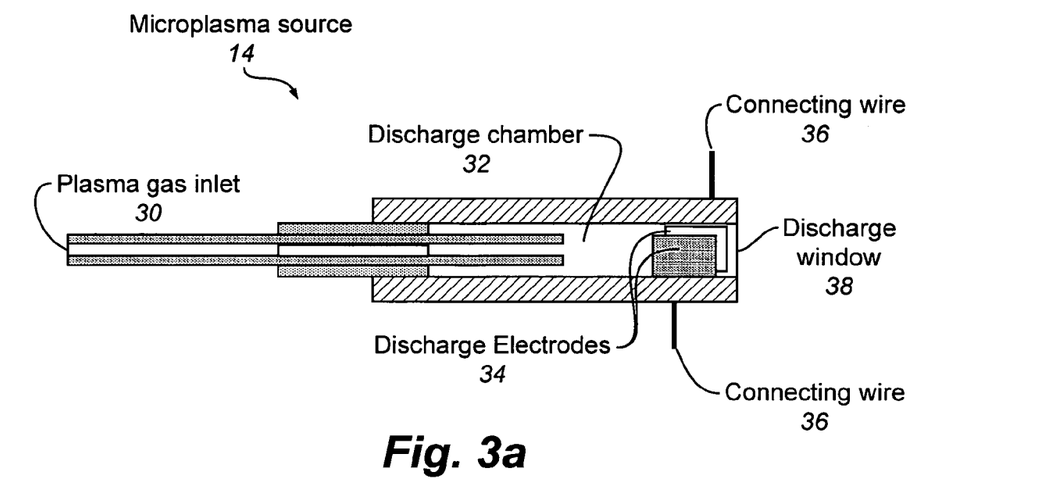
FIG. 3a-b show a side view sketch and an end view sketch, respectively, of an embodiment plasma source used with the invention.
Figure 3B:
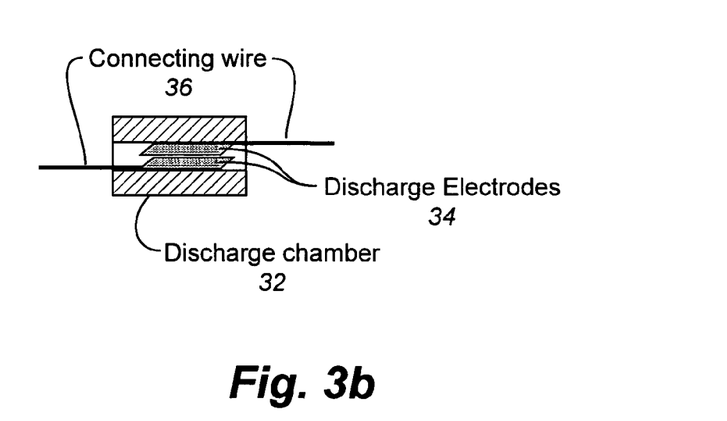

FIGS. 3a and 3b show a side view sketch and an end view sketch, respectively, of an embodiment microplasma source. As shown in FIGS. 3a-b, microplasma source 14 includes inlet 30 for plasma gas and sample to enter from the sampling line 13 (see FIG. 2). Microplasma source 14 includes a discharge chamber 32. Plasma gas entering discharge chamber 32 it is subjected to a potential from discharge electrodes 34 sufficient for converting at least a portion of the plasma gas into plasma. Microplasma source 14 also includes connecting wires 36, which connect electrodes 32 to power supply system 16 (see FIG. 2). Plasma generated in microplasma source 14 interacts with sample (acetone, for example) such that sample is fragmented and the fragments are excited and emit light that exits microplasma source through discharge window 38, and is collected and transmitted to a spectrometer. The microplasma source design is based somewhat on previous designs such as those described in the following references: Jin et al., Anal. Chem. (2001), vol. 73, pp. 360-365; Duan et al., Review of Scientific Instruments, (2003), vol. 74, pp. 2811-2816; and Jin et al., Review of Scientific Instruments (2003), vol. 74, pp. 5156-5160, all hereby incorporated by reference. In these prior designs, either rubber tubing or TEFLON tubing is used for fabricating the plasma chamber walls. An advantage of using these flexible, organic-based materials is related to the relative ease in fabricating a desired shape, the ease in electrode installation, the ease in machining and handling, and the convenience for making electrical connections. A downside is that these materials place certain limitations on the apparatus. For example, the plasma chamber may expand and change its original shape when it is heated by the discharge, which may significantly influence the stability of the plasma source. This is undesirable, because an unstable plasma source degrades the system performance. Also, the prior art materials limit the lifetime of the discharge devices due to the low tolerance of organic materials to the heat generated by the plasma source. In some cases, organic materials may create unwanted background emission and generate potentially interfering emission signals. With these limitations in mind, a preferred microplasma source of the invention employs ceramic materials. Other preferred design changes include a mechanical fixation of discharge electrodes 34 on the discharge chamber wall, a well-defined restriction of the discharge area and volume, and a better focused gas flow channel for the discharge. The plasma tolerance and stability are improved when ceramic materials are used instead of the prior art materials because they are more tolerant of the heat generated by the plasma source.

The electrodes 34 of embodiment microplasma source 14 shown in FIG. 3a-b are two small flat electrodes placed face to face. The total discharge produced using these electrodes is preferably at about the microliter level. The microplasma can be maintained at atmospheric pressure with just a small amount of plasma gas (argon or helium, for example). Since the microplasma is sustained in a very small volume, efficient collection of the optical emission beam is important for the system performance.

Figure 4A:
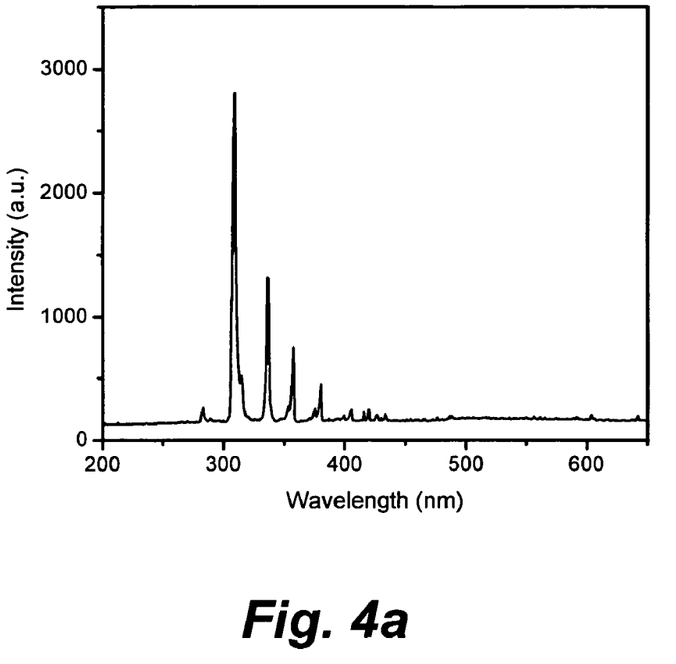
FIG. 4a-b show molecular emission spectra for (a) background, and (b) acetone using an embodiment apparatus of the present invention. The operation power used was about 700 volts; the current was about 5.0 milliamperes (mA); the plasma gas flow rate was about 1 liter per minute, and the sample volume was about 1.0 milliliter (ml).
Figure 4B:
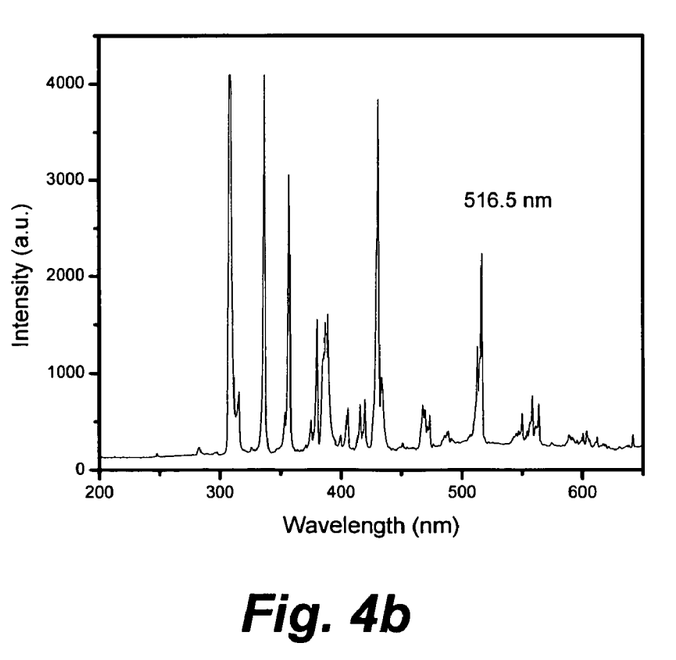

An emission spectrum of background (without introduction of sample), and a typical emission spectrum of acetone produced using the embodiment microplasma source are shown in FIGS. 4a and 4b, respectively. The acetone spectrum shown in FIG. 4b includes several peaks centered at about 516.5 nm. The peak at 516.5 nm was used as a handle for detecting acetone in breath samples. Neither moisture vapor or room air components appear to contribute to the 516.5 nm signal. While this peak was used for analysis certain embodiments of the invention, it should be understood that other peaks in the emission spectrum could also be used.

Figure 5:
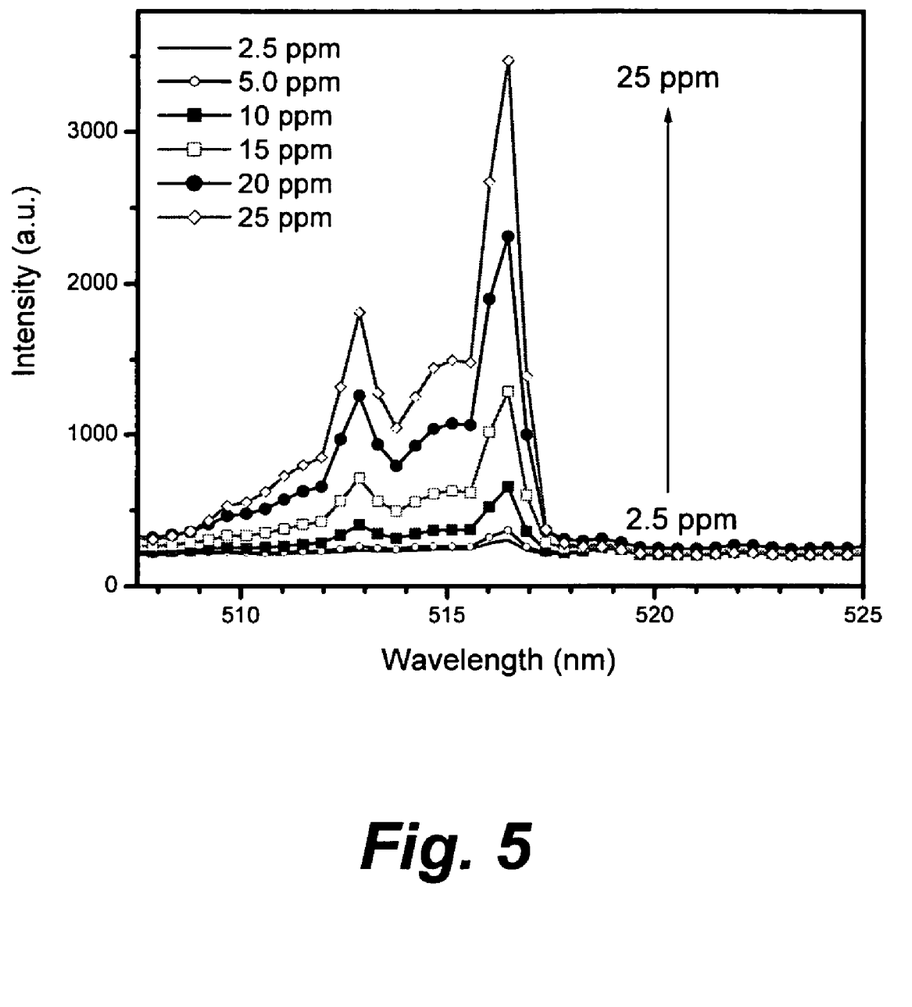
FIG. 5 shows a plot of intensity vs. wavelength for several concentrations of acetone. The operational parameters are those of FIG. 4.

The apparatus was calibrated using a series of acetone standards prepared from a gas mixture having an initial acetone concentration of 25 ppm mixed with argon. More dilute concentrations were produced using mass flow controllers. FIG. 5 shows a plot of concentration of acetone vs. signal intensities for each of the standards. As shown in FIG. 5, the acetone signal intensity increases as the concentration of acetone increases.

Figure 6:
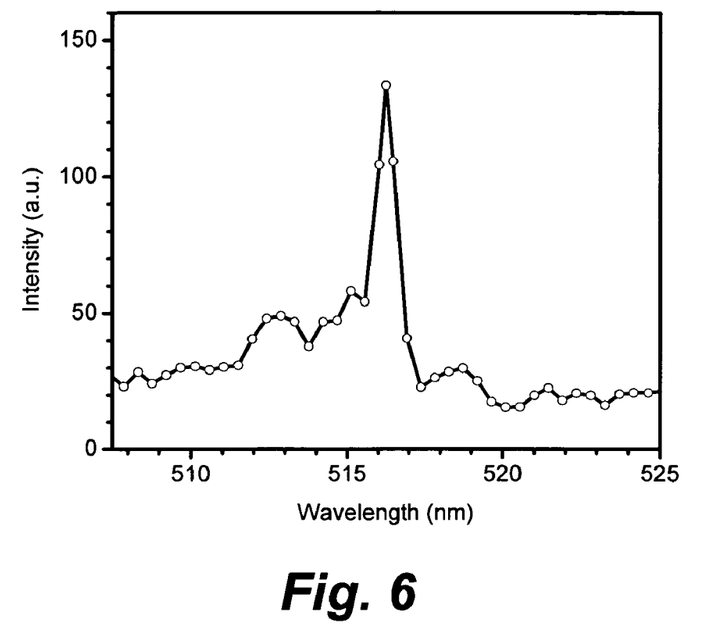
FIG. 6 shows a portion of an emission spectrum of acetone (625 ppb) in the region of about 508 nm to about 525 nm. Some of the operational parameters are: operational power: 800 V; current: 5.7 mA; and injected sample volume: 1.0 ml.

FIG. 6 shows a portion of typical acetone emission spectrum from about 508 nm to about 525 nm. The concentration of acetone used (625 ppbv) gave a net signal intensity of about 100 counts. From this, a detection limit of the embodiment microplasma emission system was estimated at about 15 ppbv, which is sufficient for breath acetone analysis. By comparison, the breath acetone level for healthy people is typically in the range of from about 200 ppbv to about 600 ppbv. Early stages of diabetes produce higher values than these.

Exhaled alveolar breath air was used for breath sampling. Exhaled breath includes two major components. The first 150 milliliters or so of breath is called "dead-space air" and comes from the trachea and the bronchioles where there is not gas exchange between the blood and breath air. The remaining part of the breath, about 350 milliliters, is the "alveolar" breath, which comes from deep in the lungs and is the part of the breath that has undergone gaseous exchange with the blood. Normal human alveolar breath contains a large number of VOCs derived from the blood by passive diffusion across the pulmonary alveolar membrane.

Breath samples of alveolar air from two healthy subjects were collected using latex gloves. Each subject exhaled alveolar breath air into a glove, and a portion of each breath sample was rapidly transferred from the glove to a syringe injector, and then injected into the apparatus. The entire sampling process from blowing into the glove, injecting the sample into the apparatus, and obtaining an emission spectrum from the sample was completed in less than about a minute.

Figure 7:
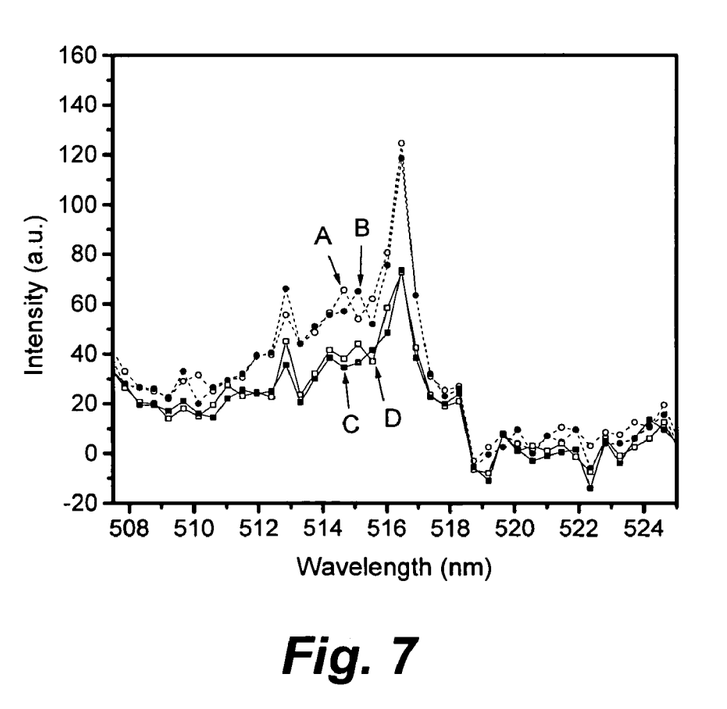
FIG. 7 shows emission spectra for breath acetone from two subjects in duplicates. Operational parameters include: operational power: 700 V; current: 5.0 mA; plasma gas flow rate: 1 L/min; and breath sample volume: 1.0 ml.

FIG. 7 shows duplicate emission spectra for breath acetone from the two subjects. Spectra A and B are spectra of breath samples from one of the subjects, and spectra C and D are from the other subject. It is clear from the duplicate analysis that the spectra obtained are highly reproducible.

The breath acetone level of healthy people is usually lower than that of people with diabetes, so we are confident that our monitoring device is also useful for breath analysis of people with diabetes.

Figure 8:
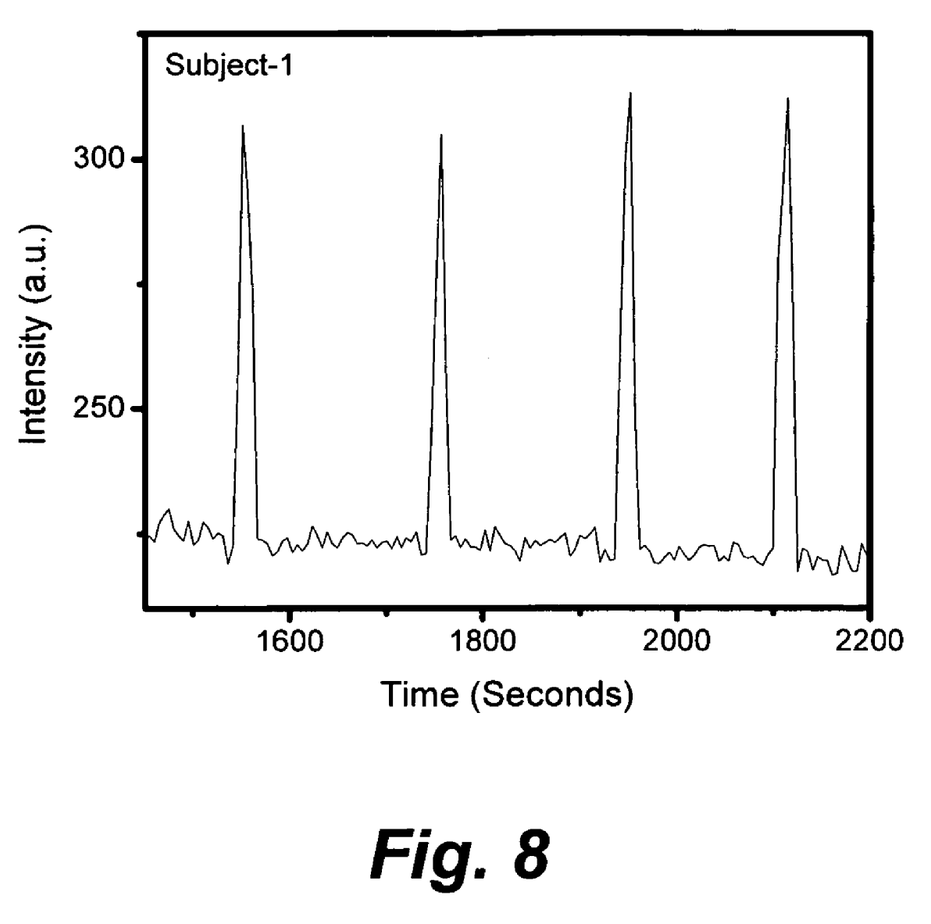
FIG. 8 shows multiple parallel breath acetone tests for a subject, with time-based scale. Operational parameters include: operational power: 700 V; current: 5.0 mA; plasma gas flow rate: 1 L/min; and breath sample volume: 1.0 ml

A time-related spectrum (see FIG. 8 for a time-related spectrum from one of the human subjects) of signal intensity versus time may also be obtained. This type of spectrum may be useful for monitoring changes in the level of breath acetone throughout the day. Changes and trends of breath acetone levels with the time, diets, overnight fasting, and meals, for example, may be identified using the present invention. The time-based experimental data could be used to explore a possible relationship between acetone level and daily activities. Time-based acetone level monitoring may also provide a better approach for effectively monitoring of diabetes and even for patient treatment.

In summary, a breath acetone monitor apparatus based on microplasma emission measurements and injection sampling has been invented. The breath acetone monitor provides capabilities for acetone measurement. The detection limit at low ppbv levels achieved with this invention is comparable to that reported using complex laboratory instruments. The invention is an important advance for breath acetone analysis for diabetes diagnostics and monitoring. The apparatus and method of the invention are noninvasive and can be used without discomfort or pain to the patient. They provide a fast response, with minimal interference in the breath gas matrix, and are sensitive enough for direct detection of breath acetone even for healthy people. The large amount of water vapor in the breath does not interfere with the analysis of real breath samples. The apparatus of the invention may be integrated into a handheld device for daily and family use and routine diabetes monitoring.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. Although the invention has been disclosed with reference to its preferred embodiments, lo from reading this description those of skill in the art can appreciate changes and modifications that may be made which do not depart from the scope and spirit of the invention as described above and claimed hereafter. It is intended that the scope of the invention be defined by the claims appended hereto.

What is claimed is:

1. A method for monitoring breath gas comprising:
   providing sufficient energy from an atmospheric pressure plasma to a sample of breath gas to fragment and excite acetone in the breath gas, thereby generating light emission from the sample of breath gas;
   directing the light emission to a spectrometer to generate an emission spectrum; and
   analyzing the emission spectrum to determine the amount of acetone in the sample of breath gas.

2. The method of claim 1, wherein the atmospheric pressure plasma comprises a microplasma.

3. The method of claim 1, wherein the step of analyzing the emission spectrum to determine the amount of acetone in the sample of breath gas involves using the peak at 516.5 nanometers as a handle for detecting acetone in breath gas.

4. A method for monitoring breath acetone, comprising:
   sending a sample of breath gas through atmospheric pressure plasma to excite and fragment volatile organic compounds in the sample and generate light emission therefrom;
   directing at least a portion of the emitted light to a spectrometer;
   using the spectrometer to produce a spectrum of the emitted light; and
   analyzing the spectrum of the emitted light to determine the amount of breath acetone in the sample.

5. The method of claim 4, wherein the atmospheric pressure plasma comprises a microplasma.

6. The method of claim 5, wherein the step of analyzing the spectrum of the emitted light to determine the amount of breath acetone in the sample involves using the peak at 516.5 nanometers as a handle for detecting acetone in breath gas.

* * * * *